United States Patent
Gueniche et al.

(10) Patent No.: US 10,555,882 B2
(45) Date of Patent: *Feb. 11, 2020

(54) MONOUNSATURATED FATTY ACID FOR NAILCARE

(71) Applicants: L'OREAL, Paris (FR); SOCIÉTÉ DES PRODUITS NESTLÉ S.A., Vevey (CH)

(72) Inventors: Audrey Gueniche, Rueil Malmaison (FR); Isabelle Castiel, Nice (FR); Cristina Cruz-Hernandez, Epalinges (CH); Marjorie Marie-Carmen Guitard, Savigny (CH); Frédéric Destaillats, Servion (CH)

(73) Assignees: L'OREAL, Paris (FR); SOCIÉTÉ DES PRODUITS NESTLÉ S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/357,335

(22) PCT Filed: Nov. 8, 2012

(86) PCT No.: PCT/IB2012/056262
§ 371 (c)(1),
(2) Date: May 9, 2014

(87) PCT Pub. No.: WO2013/068960
PCT Pub. Date: May 16, 2013

(65) Prior Publication Data
US 2014/0322187 A1    Oct. 30, 2014

(30) Foreign Application Priority Data
Nov. 9, 2011 (FR) ..................... 11 60199

(51) Int. Cl.
| *A61K 8/36* | (2006.01) |
|---|---|
| *A61K 8/92* | (2006.01) |
| *A61K 8/99* | (2017.01) |
| *A61Q 3/00* | (2006.01) |

(52) U.S. Cl.
CPC .............. *A61K 8/361* (2013.01); *A61K 8/922* (2013.01); *A61K 8/99* (2013.01); *A61Q 3/00* (2013.01); *A61K 2800/92* (2013.01)

(58) Field of Classification Search
None
See application file for complete search history.

(56) References Cited

U.S. PATENT DOCUMENTS

| 3,395,236 A | 7/1968 | White |
|---|---|---|
| 4,097,604 A | 6/1978 | Thiele |
| 6,139,852 A | 10/2000 | Takeoka et al. |
| 6,270,811 B1 | 8/2001 | Fregonese |
| 6,331,569 B1 | 12/2001 | Kisters et al. |
| 6,362,221 B1 | 3/2002 | Clark et al. |
| 6,365,175 B1 | 4/2002 | Alaluf et al. |
| 2002/0034485 A1 | 3/2002 | Noser et al. |
| 2003/0054015 A1 | 3/2003 | Haze et al. |
| 2005/0175565 A1 | 8/2005 | Duranton et al. |
| 2006/0068046 A1 | 3/2006 | Arita et al. |
| 2006/0269508 A1* | 11/2006 | Trejo ................ A23L 1/3008 424/74 |
| 2008/0248130 A1 | 10/2008 | Rath et al. |
| 2008/0319071 A1 | 12/2008 | Raederstorff et al. |
| 2009/0169652 A1* | 7/2009 | Osborne ............. A61K 8/4973 424/727 |
| 2010/0022648 A1 | 1/2010 | Gueniche et al. |
| 2010/0291012 A1* | 11/2010 | Guy ................... A61K 31/5375 424/61 |
| 2011/0008308 A1 | 1/2011 | Taylor et al. |
| 2012/0308586 A1* | 12/2012 | Garcia Villarrubia ....................... A61K 36/63 424/184.1 |
| 2013/0302297 A1 | 11/2013 | Gueniche et al. |

FOREIGN PATENT DOCUMENTS

| BE | 1019927 A3 | 2/2013 |
|---|---|---|
| CN | 101265177 A | 9/2008 |
| CN | 101453914 A | 6/2009 |
| CN | 102 293 312 A | 12/2011 |
| DE | 100 35 735 A1 | 9/2001 |
| DE | 103 25 159 A1 | 12/2003 |
| DE | 10 2005 057292 A1 | 6/2007 |
| EP | 0 116 439 A2 | 8/1984 |
| EP | 0 355 842 A2 | 2/1990 |
| EP | 0 679 383 A1 | 11/1995 |
| EP | 0 709 084 A2 | 5/1996 |
| EP | 0 888 773 A1 | 1/1999 |
| EP | 1 013 178 A1 | 6/2000 |
| EP | 1 932 509 A1 | 6/2008 |

(Continued)

OTHER PUBLICATIONS

Menon, K.N. et al. 1953. Petroselinic acid: occurrence in some umbelliferae seed fats. Proceedings of the Indian Academy of Sciences, Section A, 38(2): 128-131. specif. p. 128.*
Spangenberg, J.E. et al. 2001. Authentication of vegetable oils by bulk and molecular carbon isotope analyses with emphasis on olive oil and pumpkin seed oil. Journal of Agricultural and Food Chemistry 49: 1534-1540. specif. pp. 1534, 1536.*
Lawry, M. 2007. Biological therapy and nail psoriasis. Dermatologic Therapy 20: 60-67. specif. p. 61.*
Ramadan, M.F. et al. 2002. Oil composition of coriander (*Coriandrum sativum* L.) fruit-seeds. European Food Research and Technology 215: 204-209. specif. p. 204.*
van de Kerkhof, P.C.M. et al. 2005. Brittle nail syndrome: a pathogenesis-based approach with a proposed grading system. Journal of the American Academy of Dermatology 53: 644-651. specif. pp. 644, 645.*
Kitahara, T. et al. 1993. Coexpression of keratins characterisitic of skin and hair differentiation in nail cells. Journal of Investigative Dermatology 100: 171-175. specif. p. 171.*

(Continued)

*Primary Examiner* — Renee Claytor
*Assistant Examiner* — Sharon M. Papciak
(74) *Attorney, Agent, or Firm* — Oliff PLC

(57) ABSTRACT

The invention relates to the cosmetic use of an effective amount of at least one monounsaturated fatty acid, of a salt thereof and/or of an ester thereof, as a nailcare active agent.

7 Claims, 1 Drawing Sheet

(56) References Cited

FOREIGN PATENT DOCUMENTS

| | | |
|---|---|---|
| FR | 1 603 765 | 7/1971 |
| FR | 2 569 347 A1 | 2/1986 |
| FR | 2 756 181 A1 | 5/1998 |
| FR | 2 939 040 A1 | 6/2010 |
| FR | 2 952 304 A1 | 5/2011 |
| GB | 2 458 466 A | 9/2009 |
| JP | 59172411 A | 9/1984 |
| JP | A-1-275514 | 11/1989 |
| JP | 2005-126405 A | 5/2005 |
| WO | 99/40955 A2 | 8/1999 |
| WO | 9947110 A1 | 9/1999 |
| WO | 01/08651 A1 | 2/2001 |
| WO | 02/07700 A2 | 1/2002 |
| WO | WO 03/020249 A1 | 3/2003 |
| WO | 03/075941 A1 | 9/2003 |
| WO | 2004/000293 A2 | 12/2003 |
| WO | 2007/122382 A2 | 11/2007 |
| WO | 2008/071897 A2 | 6/2008 |
| WO | WO 2010/080915 A1 | 7/2010 |
| WO | 2012/059880 A1 | 5/2012 |
| WO | 2013/068960 A2 | 5/2013 |

OTHER PUBLICATIONS

Lynch, M.H. et al. 1986. Acidic and basic hair/nail ("hard") keratins: their colonization in upper cortical and cuticle cells of the human hair follicle and their relationship to "soft" keratins. Journal of Cell Biology 103(6), Pt. 2: 2593-2606. specif. pp. 2596, 2597, 2604.*
Database GNPD [Online] Mintel; Nov. 2011, "Skin, Hair and Nails Food Supplement", XP002678758.
Database GNPD [Online] Mintel; May 2010, "Cold Pressed Flaxseed Oil", XP002678759.
Database GNPD [Online] Mintel; Oct. 2009, "Essential Seed Omega Shake", XP002678760.
Database GNPD [Online] Mintel; Nov. 2005, "Organic Omega Seed Oil", XP002678761.
Database GNPD [Online] Mintel; Aug. 2005, "Energizing Drink Mix", XP002678762.
Database GNPD [Online] Mintel; Mar. 2008, "Lactobacillus Supplement", XP 002678763.
International Search Report issued in International Patent Application No. PCT/IB2012/056262 dated Mar. 31, 2014.
Written Opinion issued in International Patent Application No. PCT/IB2012/056262 dated Mar. 31, 2014.
Written Opinion issued in French Patent Application No. 1160199 dated Nov. 9, 2011 (with partial translation).
Oct. 17, 2016 Office Action issued in U.S. Appl. No. 14/889,984.
Oct. 20, 2016 Office Action issued in U.S. Appl. No. 14/889,895.
Nov. 1, 2016 Office Action issued in U.S. Appl. No. 12/518,959.
U.S. Appl. No. 14/889,895, filed Nov. 9, 2015 in the name of Mahe et al.
U.S. Appl. No. 14/890,071 filed Nov. 9, 2015 in the name of Mahe et al.
Oct. 21, 2014 Search Report issued in International Patent Application No. PCT/IB2014/061247.
Oct. 21, 2014 Written Opinion issued in International Patent Application No. PCT/IB2014/061247.
Jul. 8, 2014 Search Report issued in International Patent Application No. PCT/IB2014/061235.
Jul. 8, 2014 Written Opinion issued in International Patent Application No. PCT/IB2014/061235.
Lacasa, Daniéle et al. "Macrophage-Secreted Factors Impair Human Adipogenesis: Involvement of Proinflammatory State in Preadipocytes." Endocrinology, vol. 148 No. 2, pp. 868-877, 2007.
Keophiphath, Mayoura et al. "Macrophage-Secreted Factors Promote a Profibrotic Phenotype in Human Preadipocytes." Molecular Endocrinology vol. 23, No. 1, pp. 11-24, 2009.
Salminen, S. et al. "Probiotics: How Should They Be Defined?" Trends in Food Science and Technology, vol. 10, pp. 107-110, 1999.
Gibson R., Glenn and Roberfroid B., Marcel, "Dietary Modulation of the Human Colonic Microbiota: Introducing the Concept of Prebiotics". The Journal of Nutrition, vol. 125, pp. 1401-1412, 1995.
Avato, Pinarosa et al. "The Genus Thapsia as a Source of Petroselinic Acid". Lipids, vol. 36, No. 8, pp. 845-850, 2001.
Jul. 8, 2014 Search Report issued in International Patent Application No. PCT/IB2014/061264.
Jul. 8, 2014 Written Opinion issued in International Patent Application No. PCT/IB2014/061264.
Oct. 21, 2014 Search Report issued in International Patent Application No. PCT/IB2014/061245.
Oct. 21, 2014 Written Opinion issued in International Patent Application No. PCT/IB2014/061245.
Destaillats, Frédéric et al. "Identification of 6-Monosaturated Fatty Acids in Human Hair and Nail Samples by Gas-Chromatography-Mass-Spectrometry Using Ionic-Liquid Coated Capillary Column". Journal of Chromatography A, Elsevier Science Publishers B.V, NL, vol. 1218, No. 52, pp. 9384-9389, 2011.
Singh, Vivek et al. "Availability of Essential Trace Elements in Indian Cereals, Vegetables and Spices Using INAA and the Contribution of Spices to Daily Dietary Intake". Food Chemistry, Elsevier Ltd, NL, vol. 94, No. 1, pp. 81-89, 2006.
Oct. 21, 2014 Search Report issued in International Patent Application No. PCT/IB2014/061246.
Oct. 21, 2014 Written Opinion issued in International Patent Application No. PCT/IB2014/061246.
Placek et al., "A Review on Petroselinic Acid and its Derivatives". Journal of the American Oil Chemists' Society, vol. 40, No. 8, pp. 319-329, 1963.
Xu et al., "The Potential Health Benefits of Taurine in Cardiovascular Disease". Experimental Clinical Cardiology: Review, vol. 13, No. 2, pp. 57-65, 2008.
Tsuboyama-Kasaoka et al., "Taurine (2-Aminoethanesulfonic Acid) Deficiency Creates a Vicious Circle Promoting Obesity". Endocrinology, vol. 147, No. 7, pp. 3276-3284, 2006.
Jun. 16, 2016 Office Action issued in U.S. Appl. No. 14/889,984.
Aug. 8, 2016 Office Action issued in U.S. Appl. No. 14/890,071.
Bernard, "La Vie Révélée Du Follicule De Cheveu Humain". Médecine Sciences, vol. 22, No. 2, pp. 138-143, 2006.
Mar. 29, 2012 Office Action issued in U.S. Appl. No. 12/518,959.
Jan. 25, 2013 Office Action issued in U.S. Appl. No. 12/518,959.
Jul. 31, 2014 Office Action issued in U.S. Appl. No. 12/518,959.
Feb. 16, 2016 Office Action issued in U.S. Appl. No. 12/518,959.
Mar. 12, 2015 Office Action issued in U.S. Appl. No. 12/518,959.
Monnier et al., "Nonenzymatic Glycosylation and Browning of Proteins In Vivo". American Chemical Society, pp. 431-449, 1983.
Jaworksy et al., "Characterization of Inflammatory Infiltrates in Male Pattern Alopecia: Implications for Pathogenesis". British Journal of Dermatology, vol. 127, pp. 239-246, 1992.
Sueki et al., "Quantitative and Ultrastructural Analysis of Inflammatory Infiltrates in Male Pattern Alopecia". Acta Derm Venereol, vol. 79, pp. 347-350, 1999.
Tsevegsuren et al., "Geranium Sanguineum (*Geraniaceae*) Seed Oil: A New Source of Petroselinic and Vernolic Acid". Lipids, vol. 39, No. 6, pp. 571-576, 2004.
U.S. Appl. No. 14/890,064, filed Nov. 9, 2015 in the name of Mahe et al.
U.S. Appl. No. 14/890,069 filed Nov. 9, 2015 in the name of Mahe et al.
May 11, 2016 Office Action issued in U.S. Appl. No. 14/890,064.
U.S. Appl. No. 14/889,984, filed Nov. 9, 2015 in the name of Mahe et al.
U.S. Appl. No. 12/518,959, filed Sep. 24, 2009 in the name of Gueniche et al.
Jun. 13, 2017 Office Action Issued in U.S. Appl. No. 14/889,984.
Jun. 21, 2017 Office Action Issued in U.S. Appl. No. 12/518,959.
Nov. 16, 2017 Office Action issued in U.S. Appl. No. 14/890,069.
Jan. 30, 2017 Office Action issued in U.S. Appl. No. 14/890,064.
Burdock, George A. et al. "Safety Assessment of Coriander (*Coriandrum sativum* L.) Essential Oil as a Food Ingredient". Food and Chemical Toxicology, 2009, vol. 47, pp. 22-34.

(56) References Cited

OTHER PUBLICATIONS

Story, Erica N. et al. "An Update on the Health Effects of Tomato Lycopene." Annual Review of Food Science and Technology, 2010, vol. 1, pp. 189-210.
Feb. 27, 2017 Office Action issued in Chinese Patent Application No. 201480038812.3.
Cheng, Hong-Yan et al. "Genetic Modifications on Industrial Characteristics of Seed Oils." Acta Botanica Yunnanica, vol. 30, No. 1, 2008, pp. 89-94.
Apr. 20, 2017 Office Action Issued in U.S. Appl. No. 14/890,069.
Apr. 3, 2018 Office Action issued in U.S. Appl. No. 14/890,064.
Apr. 5, 2018 Office Action issued in U.S. Appl. No. 12/518,959.
Aug. 29, 2018 Office Action issued in U.S. Appl. No. 14/890,069.
Nan, Jinming et al. "Yu County SPA Recuperation Guidelines." Shanxi People's Publishing House, Edition 1, 1994, pp. 65-66.
Greenberg et al. "Obesity and the Role of Adipose Tissue in Inflammation and Metabolism" Am J Clin Nutr. 2006; 83 (Suppl) 461S-5s (Year:2006).
Jan. 7, 2019 Office Action issued in U.S. Appl. No. 12/518,959.
Dec. 11, 2018 Office Action issued in U.S. Appl. No. 14/890,064.
Feb. 28, 2019 Office Action issued in U.S. Appl. No. 14/890,069.
Borgeson, Emma et al., "Lipdxin A4 Attenuates Adipose Inflammation", (2012), The FASEB Journal, vol. 26: p. 4287-4294.
Nov. 5, 2019 Office Action issued in U.S. Appl. No. 12/518,959.

\* cited by examiner

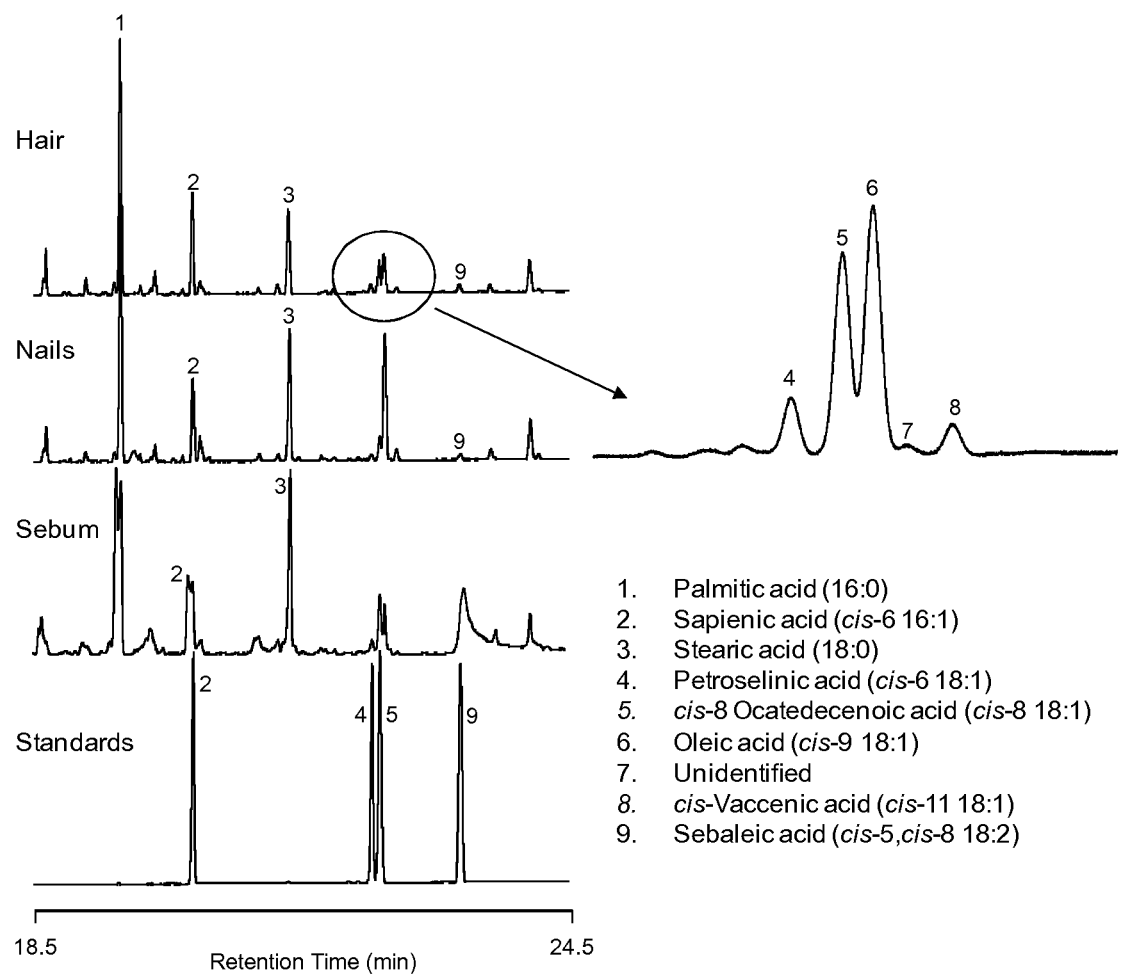

MONOUNSATURATED FATTY ACID FOR NAILCARE

The present invention relates to the field of cosmetic and/or dermatological products and food supplements intended for nailcare.

More particularly, the present invention proposes the use of a novel active agent for treating and/or preventing esthetic defects, and/or reinforcing and/or improving the growth, the solidity or the hardness of nails. The present invention also relates to a process for nailcare, and in particular for treating and/or preventing esthetic defects of nails, and/or for reinforcing and/or improving the growth, the solidity or the hardness of nails.

A nail or ungual plaque is a flexible, smooth and translucent horny blade which forms a surface excrescence of the skin, consisting of keratinocytes and a very dense and homogeneous keratin matrix. This matrix keeps the cells welded together and gives the nail its strength, hardness, solidity and flexibility. The nail is enveloped by an epidermal sheath, or matrix. It is at this level that the formation of the cells giving rise to the nail takes place. A healthy nail grows on average by 0.10 mm per day. Its growth is continual.

From a morphological viewpoint, a nail consists of a dorsal part, an intermediate part, a ventral part, a proximal matrix, an intermediate matrix, a lunula and the nail bed. 80% of the thickness of a nail is produced by the proximal matrix, and 20% of its thickness is produced by the intermediate matrix and the nail bed. The dorsal part consists of hard keratin, the intermediate part is the thickest and is formed of moderately hard keratin, and the ventral part consists of soft keratin.

As regards its chemical constitution, a nail contains water, lipids, mucopolysaccharides and minerals, such as sodium, potassium, iron, calcium, zinc or silicon.

The hardness and flexibility of nails depends especially on the orientation of the keratin fibres, the arrangement of the keratinocytes and their cohesion and chemical constitution, in particular the content of water, lipids and phospholipids.

Many factors may impair the chemical constitution of nails and, as a result, their growth, their hardness or their shape, or may give rise to tint or color imperfections.

Among the extrinsic factors that are liable to affect the nails, mention may be made of exposure to sunlight, exposure to temperature and/or humidity variations, and exposure to pollutants or to cigarette smoke. Among the intrinsic factors affecting the nails, mention may be made of stress, fatigue, hormonal changes, dehydration, a metabolic deficit, aging or certain pathological conditions.

In particular, external attacks associated with exposure to water, to soap or to various detergents has a tendency to deplete the nails of the lipids provided by the cuticles. As it happens, these lipids, which travel in the nail by means of its porous structure, contribute toward its flexibility, its solidity and its resistance to breaking.

These various factors are liable to affect the growth of the nails, make them fragile or brittle, affect their shape, color or tint, and thus greatly reduce their esthetic appearance.

At the present time, the main solutions proposed in the field of nailcare are based on the use of nail varnishes, of moisturizing active agents in handcare products, or of chemical reinforcement of the nail. The latter solution is based on the use of nail-hardening agents, such as formaldehyde at 1-2%, which generate crossbonds in the keratin. However, frequent use of these products may give rise to too many crossbonds, paradoxically promoting embrittlement of the nails.

Biological treatments, or the use of ingredients for stimulating nail growth, such as calcium, fluorine, trace elements or vitamins, have also been proposed.

However, hitherto and to the inventors' knowledge, no solution exists that acts directly on the liquid composition of the nails, which are very sensitive to the various forms of external attack.

From a cosmetic viewpoint, there is thus a need to be able to prevent, reduce or treat the various impairments that may affect the nails, irrespective of the origin of these impairments.

There is also a need for novel active agents that can exert efficient and beneficial action on the nails, and in particular on their growth, their hardness, their resistance to impacts or to external attacking factors, their smooth appearance, and consequently their esthetic appearance.

There is also need to be able to overcome the lipid deficiencies of the nails, which are liable to arise from their exposure to various external factors.

The object of the present invention is to satisfy these needs.

Thus, according to a first aspect, the present invention relates to a cosmetic use of at least one monounsaturated fatty acid, a salt thereof and/or an ester thereof, as a nailcare active agent.

Monounsaturated fatty acids have been described for various applications, such as the moisturization of dry skin in EP 0 709 084 or the treatment of dandruff and itchy scalps in EP 0 116 439.

To the inventors' knowledge, the presence of monounsaturated fatty acids, especially of petroselinic acid, in the nails has never been revealed hitherto. Thus, to the inventors' knowledge, it has never been proposed or suggested that the administration, as an active agent, of at least one monounsaturated fatty acid, especially petroselinic acid, to an individual in need thereof could prove to be particularly effective for nailcare.

Thus, and as shown in the examples, an individual treated according to the invention may advantageously observe a reduction in, or even disappearance of, his nails' impairments. The nails become harder, less brittle, more flexible, more resistant to impacts, and have a smooth, translucent appearance and a uniform color and tint.

Advantageously, these fatty acids make it possible to overcome the lipid deficiencies induced by the various forms of external attack, and especially by exposure to water, to soap or to various detergents, since they tend toward reproducing the natural lipids of the nails.

Advantageously also, the invention makes it possible to reinforce the nails and to improve their esthetic appearance.

A use according to the invention can be carried out orally.

According to another of its aspects, a subject of the present invention is a cosmetic treatment process for nailcare, in the case of an individual in need thereof, comprising at least one step of administering to said individual, as an active agent, at least one monounsaturated fatty acid, a salt thereof and/or an ester thereof. A process of the invention is carried out orally.

The present invention advantageously makes it possible to prevent and/or treat nail imperfections.

According to one embodiment, the invention advantageously makes it possible to prevent and/or treat brittle, fragile, soft, split or cracked nails.

According to another embodiment, the invention advantageously makes it possible to prevent and/or treat nails having a striated surface appearance, or to reduce the presence or depth of the nail striations, or to improve the smooth surface appearance of the nails.

According to another embodiment, a use in accordance with the invention advantageously makes it possible to prevent and/or treat a nonuniform color or tint or a dull appearance of the nails, or even to improve or reinforce a white color or tint of the nails.

A monounsaturated fatty acid according to the invention is necessarily used in an effective amount, i.e. an amount that enables the fatty acid to manifest its active properties with regard to the care to be afforded to the nails.

For the purposes of the present invention, the term "prevent" means reducing to a lesser extent the risk or probability of manifestation of a given phenomenon, i.e. in the present invention impairment of the nails.

Monounsaturated Fatty Acid

For the purposes of the present invention, the term "monounsaturated fatty acid" means a fatty acid whose hydrocarbon-based chain comprises only one double bond, and which is in a free form.

They are more particularly fatty acids containing long hydrocarbon-based chains. The monounsaturated fatty acids that are suitable for use in the invention are especially monounsaturated fatty acids comprising a hydrocarbon-based chain containing from 12 to 22 carbon atoms.

The monounsaturated fatty acids that are suitable for use in the invention may be used in acid form or in salt form, or alternatively in the form of derivatives, especially fatty acid esters and amides.

When they are in the form of salts, the monounsaturated fatty acids of the invention are more particularly cosmetically acceptable salts, i.e. inorganic salts, such as ammonium salts, salts of alkali metals such as lithium, potassium or sodium, salts of alkaline-earth metals such as magnesium or calcium, or aluminum salts.

In particular, the monounsaturated fatty acids that are suitable for use in the invention may be in the form of calcium salts.

When they are in the form of esters, the monounsaturated fatty acids of the invention may be esterified with glycerol in mono-, di- or triacyl form, with an alcohol such as methyl and ethyl alcohols, with a sugar, especially a monosaccharide or a disaccharide, a tocopherol, a tocotrienol, a sterol, such as cholesterol or a phytosterol such as β-sitosterol, or with a fatty acid, especially a $C_8$ to $C_{18}$ fatty acid.

It is understood that the choice of the monounsaturated fatty acids of the invention is made taking into account the end use of the composition comprising them.

The monounsaturated fatty acid of the invention, the salt thereof and/or the ester thereof can be used in an oral composition in which the content of said monounsaturated fatty acid, the salt thereof and/or the ester thereof is such that the daily dose ranges from 0.5 to 2500 mg/d, in particular from 1 to 2000 mg/d, more particularly from 2 to 1500 mg/d, or even from 3 to 1000 mg/d, and especially from 5 to 600 mg/d.

Among the monounsaturated fatty acids that are suitable for use in the invention, use may be made more particularly of oleic acid, petroselinic acid, sapienic acid, cis-8-octadecenoic acid or cis-vaccenic acid, or mixtures thereof. Petroselinic acid is most particularly suitable for use in the invention.

According to one variant of the invention, the monounsaturated fatty acid(s) are used in an isolated form, i.e. after extraction from their source of origin.

According to another variant of the invention, the monounsaturated fatty acid(s) are used in a plant extract such as an oil.

Thus, the invention relates especially to the cosmetic use of an oil rich in monounsaturated fatty acid of the invention, and in particular rich in petroselinic acid.

The oils rich in petroselinic acid are more particularly chosen from *Umbellifera* plant oils.

The term "oil rich in petroselinic acid" means an oil comprising at least 40% petroselinic acid.

*Umbelliferae* are plants whose flowers are arranged in umbels, and the species that are particularly rich in petroselinic acid are *Umbelliferea-Apiacea* and *Araliaceae*. Plants of the genus *Thapsia* are also sources of petroselinic acid (Avato et al., Lipids, 2001, 36, 845).

The species preferably used in the invention are coriander, chervil, carrot, celery, cumin, caraway, parsley and dill, or mixtures thereof.

The *Umbellifera* plant oil used according to the invention may be extracted from the seed of an *Umbellifera* plant, for example by grinding or pressing, followed by refining.

The *Umbellifera* plant oil has a petroselinic acid content that varies according to the *Umbellifera* plant seed from which it is extracted. For the same *Umbellifera* plant, the petroselinic acid content also varies according to the country of origin of the *Umbellifera* plant and according to the extraction, which may be more or less complete.

Petroselinic acid is also an abundant compound (about 48%) of the oil from the seed of *Gernium sanguneum* (Tsevegsuren et al., Lipids, 2004, 39, 571).

According to one embodiment, the monounsaturated fatty acid more particularly under consideration in the invention is petroselinic acid.

In particular, the petroselinic acid may be used in the form of *Umbellifera* plant oil or *Gernium sanguneum* oil.

According to another embodiment, the *Umbellifera* plant oil more particularly under consideration in the invention may be chosen from the seed oils of coriander, chervil, carrot, celery, cumin, caraway, parsley and dill, or mixtures thereof.

Indications

The invention improves, reinforces or restores an esthetically healthy state of a nail.

As indicated previously, various intrinsic or extrinsic factors may be the cause of an esthetically degraded state of the nails. The object of the present invention is to restore this state without treating or preventing the cause, and is thus limited to the cosmetic field. The invention does not relate to the therapeutic field.

According to one embodiment, the invention is directed toward preventing and/or treating an impairment in the structure of the nails, in particular to prevent and/or treat brittle, fragile, soft, split or cracked nails.

For the purposes of the invention, the expression "impairment in the structure of the nails" means an impairment in the organization of the keratin fibers or of their chemical composition, especially their lipid composition, constituting the nails with regard to an organization or a composition observed in nails of healthy esthetic quality.

More particularly, the impairments in the structure of the nails may lead to the presence of striations on the surface of the nails or to a deformation of the nails. Thus, the invention is also directed toward preventing and/or treating deformed or striated nails.

According to one embodiment, the invention is also directed toward preventing and/or treating nails of nonuniform color or tint or nails which have marks or a dull appearance. In particular, the nails under consideration by the invention may have a yellowish tint or marks.

According to one embodiment, an active agent under consideration in the invention promotes, reinforces and/or improves the growth and/or flexibility and/or hardness of the nails. Nails treated according to the invention thus prove to be less brittle, harder, more flexible, and/or more resistant to impacts, and have a lesser tendency to split.

An active agent of the invention can also make the nails smooth, shiny and/or translucent.

Finally, an active agent of the invention gives the nails a whiter, shinier and/or more homogeneous color or tint.

Galenical Form

The compositions according to the invention may be administered orally. The compositions according to the invention may be in any galenical form normally used for the oral route.

A composition according to the invention comprises a physiologically or pharmaceutically acceptable medium.

The oral route has the advantage of acting in a more overall manner on the whole of the structure of the nails and of the cells involved in their formation.

The term "oral composition" means, for example, nutritional, nutraceutical or cosmeceutical compositions comprising at least one monounsaturated fatty acid according to the invention, a salt thereof and/or an ester thereof.

In the case of a composition suitable for oral administration, the use of an ingestible support is preferred. The ingestible support may be of diverse nature according to the type of composition under consideration.

For ingestion, numerous embodiments of oral compositions and especially of food supplements are possible.

The formulation of such compositions can be carried out by any usual process known to those skilled in the art for producing, for example, oral solutions, sugar-coated tablets, gel capsules, gels, emulsions, tablets to be swallowed or chewed, capsules, in particular soft or hard capsules, granules to be dissolved, syrups, solid or liquid foods and hydrogels for controlled release.

Tablets, gels or lozenges, suspensions, oral supplements in dry form and oral supplements in liquid form are suitable as food supports.

In particular, an active agent according to the invention may be incorporated into any form of food supplement or enriched food, for example food bars or compact or loose powders. The powders may be diluted with water, in soda, dairy products or soybean derivatives, or may be incorporated into food bars.

According to one preferred embodiment, a composition according to the invention administered orally may be formulated in the form of sugar-coated tablets, gel capsules, gels, emulsions, tablets, capsules, hydrogels, food bars, compact or loose powders, liquid suspensions or solutions, confectionery products, fermented milks, fermented cheeses, chewing gum, toothpaste or spray solutions.

Milk, yoghurt, cheese, fermented milks, milk-based fermented products, ice creams, fermented or nonfermented cereal-based products, milk-based powders, infant and baby formulae, animal feed in particular for pets, tablets or lozenges, liquid bacterial suspensions, oral supplements in dry form and oral supplements in liquid form are, for example, suitable as food supports.

The oral compositions may be either in anhydrous form or in aqueous form according to the dermocosmetic indication.

An active agent according to the invention may be formulated with the usual excipients and components for such oral compositions or food supplements, i.e. especially fatty and/or aqueous components, humectants, thickeners, preserving agents, texture agents, taste agents and/or coating agents, antioxidants, preserving agents and dyes that are common in the food sector.

The formulating agents and excipients for oral compositions, and especially for food supplements, are known in this field and are not the subject of a detailed description herein.

In particular, the composition according to the invention may be a food composition for human consumption. This may be, in particular, nutritional complete foods, drinks, mineral waters, soups, dietary supplements and replacement or substitute foods, nutrional bars, confectionery, milk-based products or fermented milk-based products, yoghurts, milk-based powders, enteral nutritional products, infant and/or baby compositions, fermented or nonfermented cereal-based products, ice creams, chocolate, coffee, "culinary" products such as mayonnaise, tomato puree or salad dressings.

Additional Active Agent

A monounsaturated fatty acid according to the invention may advantageously be used in combination with an additional active agent, especially a cosmetic or pharmaceutical active agent.

Advantageously, such an additional cosmetic or pharmaceutical active agent may be intended to exert a cosmetic care or hygiene effect on the nails.

The additional active agents are chosen by a person skilled in the art so that they do not harm the effect of the monounsaturated fatty acids of the invention.

As additional active agents that may be used, mention may be made of:

vitamins, such as vitamin A, $B_5$, $B_6$, $B_8$, C, D, E or PP (vitamin $B_3$ or niacin), antioxidants, such as curcuminoids; carotenoids, especially a carotenoid chosen from β-carotene, lycopene and derivatives thereof, such as cis-lycopene or lactolycopene, astaxanthin, zeaxanthin and lutein or compounds containing same, such as wolfberry or lacto-wolfberry; polyphenol compounds, flavonoids such as catechins; hesperidin, proanthocyanidins, anthocyanins, PCOs (procyannidol oligomers); ubiquinones; coffee extracts containing polyphenols and/or diterpenes; chicory extracts; *Ginkgo biloba* extracts; grape extracts rich in proanthocyanidins; pimento extracts; soybean extracts; cocoa or coconut milk; pomegranate; Emblica, minerals such as zinc, calcium, magnesium, copper, iron, iodine, manganese, selenium and chromium (III), sugars, amino acids, especially sulfur amino acids such as glutathione precursors, taurine and selenium amino acids, 3 and 6 polyunsaturated fatty acids, prebiotics, chosen especially from oligosaccharides, produced from glucose, galactose, xylose, maltose, sucrose, lactose, starch, xylan, hemicellulose, inulin, gums of acacia type, for example, or a mixture thereof. More particularly, the oligosaccharide comprises at least one fructo-oligosaccharide. More particularly, this prebiotic may comprise a mixture of fructo-oligosaccharide and of inulin.

phytosterols, such as resveratrol, hesperidin and neohesperidin, orthosilicic acid and monomethylsilanetriol, and mixtures thereof.

According to one preferred embodiment, a monounsaturated fatty acid according to the invention, a salt thereof and/or an ester thereof may be used in combination with at least one additional cosmetic active agent chosen in particular from vitamin $B_3$, $B_5$, $B_6$, $B_8$, C, E or PP, carotenoids, curcuminoids, niacin, flavonoids, orthosilicic acid, monomethylsilanetriol, or one or more divalent mineral cations, bacteria or bacterial extracts derived from non-photosynthetic and non-fructifying filamentous bacteria, probiotic microorganisms, in particular lactic acid microorganisms, prebiotic nutrients or a mixture of probiotic microorganisms and/or a mixture of prebiotic nutrients.

In particular, use may be made of an antioxidant complex comprising vitamins C and E, and at least one carotenoid, especially a carotenoid chosen from β-carotene, lycopene and derivatives (cis-lycopene, lactolycopene), astaxanthin, zeaxanthin and lutein or compounds containing same such as wolfberry or lactowolfberry, flavonoids such as catechins, hesperidin, proanthocyanidins and anthocyanins, resveratrol, cocoa or coconut milk, pomegranate and Emblica.

A composition of the invention may also contain one or more divalent mineral cations in various forms.

A divalent mineral cation may thus be in the form of an anhydrous or hydrated mineral or organic salt or a chelated complex. These salts may be, for example, carbonates, bicarbonates, sulfates, glycerophosphates, chlorides, nitrates, acetates, hydroxides, oxides, α-hydroxy acid salts (citrates, tartrates, lactates, malates) or fruit acid salts, or alternatively amino acid salts (aspartate, arginate, fumarate) or fatty acid salts (palmitate, oleate, caseinate, behenate).

A divalent mineral cation may be chosen from manganese, copper and/or zinc or from alkaline-earth metals. As alkaline-earth metals that may be used in the invention, mention may be made of barium, calcium, magnesium, strontium and/or beryllium.

Advantageously, a divalent mineral cation, and especially an alkaline-earth metal, is used in the present invention in salt form. In particular, the salt may be chosen from nitrate, citrate, chloride, gluconate, sulfate, lactate and/or acetate salts.

A divalent mineral cation may also be used in the form of a chelated complex, especially chelated to crystalline or ionized proteins.

A divalent mineral cation may also be in a specific form stored by a microorganism, for example such as a yeast, like selenium yeasts.

According to another embodiment, a composition of the invention may contain non-photosynthetic and non-fructifying filamentous bacteria or bacterial extracts derived from non-photosynthetic and non-fructifying filamentous bacteria as defined according to the classification in Bergey's Manual of Systemic Bacteriology, volume 3, section 23, 9th edition, 1989.

Mention may be made in particular of bacteria belonging to the order of Beggiatoales, and especially bacteria belonging to the genus *Beggiatoa*. Mention may moreover be made of bacteria belonging to the genus *Vitreoscilla*, which is similar to the genus *Beggiatoa*. Among the bacteria that may be used, mention may be made, for example, of *Vitreoscilla beggiatoides* (ATCC 43181) and *Beggiatoa alba* (ATCC33555), and preferentially the use of the extract of *Vitreoscilla filiformis*, in particular with the strain ATCC 15551, metabolites thereof and fractions thereof may be used.

A composition of the invention may also comprise at least one probiotic microorganism, a prebiotic agent or a mixture of probiotic microorganisms and a mixture of prebiotic agents.

Specific examples of probiotic microorganisms that are suitable for use in the invention are *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* (LC1, NCFB 1748); *Lactobacillus amylovorus, Lactobacillus casei* (Shirota), *Lactobacillus rhamnosus* (strain GG), *Lactobacillus brevis, Lactobacillus crispatus, Lactobacillus delbrueckii* (subsp. *bulgaricus, lactis*), *Lactobacillus fermentum, Lactobacillus helveticus, Lactobacillus gallinarum, Lactobacillus gasseri, Lactobacillus johnsonii, Lactobacillus paracasei, Lactobacillus plantarum, Lactobacillus reuteri, Lactobacillus rhamnosus, Lactobacillus salivarius, Lactobacillus alimentarius, Lactobacillus curvatus, Lactobacillus casei* subsp. *casei, Lactobacillus sake, Lactococcus lactis, Enterococcus faecalis* or *faecium, Lactococcus lactis* subspp. *lactis* or *cremoris, Leuconostoc mesenteroides* subsp. *dextranicum, Pediococcus acidilactici, Sporolactobacillus inulinus, Streptococcus salvarius* subsp. *thermophilus, Streptococcus thermophilus, Staphylococcus carnosus, Staphylococcus xylosus, Saccharomyces* (*cerevisiae* or *boulardii*), *Bacillus* (*cereus* var. *toyo* or *subtilis*), *Bacillus coagulans, Bacillus licheniformis, Escherichia coli* strain *nissle, Propionibacterium freudenreichii*, and mixtures thereof.

The microorganisms may be formulated in the form of powders, i.e. in a dry form, or in the form of suspensions or solutions.

More particularly, they may be probiotic microorganisms chosen from microorganisms of the genus *Lactobacillus* sp. and/or *Bifidobacterium* sp., a fraction thereof and/or a metabolite thereof. As illustrations of these microorganisms, mention may be made more particularly of *Lactobacillus johnsonii, Lactobacillus reuteri, Lactobacillus rhamnosus, Lactobacillus paracasei, Lactobacillus casei, Bifidobacterium bifidum, Bifidobacterium breve, Bifidobacterium longum, Bifidobacterium animalis, Bifidobacterium lactis, Bifidobacterium infantis, Bifidobacterium adolescentis* and *Bifidobacterium pseudocatenulatum*, and mixtures thereof.

The species that are most particularly suitable for use are *Lactobacillus johnsonii, Lactobacillus paracasei, Bifidobacterium adolescentis, Bifidobacterium longum* and *Bifidobacterium* lactis NCC 2818 (also known as Bb12 ATCC 27536), which were deposited, respectively, according to the Budapest Treaty, at the Institut Pasteur (28, rue du Docteur Roux, F-75024 Paris cedex 15) on Jun. 30, 1992, Jan. 12, 1999, Apr. 15, 1999, Apr. 15, 1999 and Jun. 7, 2005 under the following designations CNCM I-1225, CNCM I-2116, CNCM I-2168 and CNCM I-2170 and CNCM I-3446, and the genus *Bifidobacterium longum* (BB536). The strain of *Bifidobacterium lactis* CNCM 1-3446 may be obtained from Hansen (Chr. Hansen A/S, 10-12 Boege Alle, P.O. Box 407, DK-2970 Hoersholm, Denmark).

According to one particular embodiment of the invention, the composition comprises at least two different microorganisms, which are especially probiotic, and/or metabolites and/or fractions thereof. These microorganisms may differ by their nature, for example bacterium and fungus, or alternatively by their family, their genus or their species, or only by their strain.

The prebiotic agents that are suitable for use in the invention may be chosen from oligosaccharides, produced from glucose, galactose, xylose, maltose, sucrose, lactose, starch, xylan, hemicellulose, inulin, gums of acacia type, for example, or a mixture thereof. More particularly, the oligosaccharide comprises at least one fructo-oligosaccharide. More particularly, this prebiotic may comprise a mixture of fructo-oligosaccharide and of inulin.

A composition of the invention may also advantageously contain polyunsaturated fatty acids chosen especially from ω-3 fatty acids and ω-6 fatty acids.

In particular, the unsaturated fatty acids that are suitable for use in the invention may be chosen from fatty acids comprising from 18 to 22 carbon atoms, in particular polyunsaturated fatty acids, and especially ω-3 and ω-6 fatty acids.

Among the polyunsaturated fatty acids of the ω-6 series that may be used in a composition of the invention, mention may be made in particular of linoleic acid containing 18 carbon atoms and two unsaturations (18:2 ω-6), γ-linolenic acid containing 18 carbon atoms and three unsaturations (18:3 ω-6), di-homo-γ-linolenic acid containing 20 carbon atoms and three unsaturations (20:3 ω-6), arachidonic acid (20:4 ω-6) and docosatetraenoic acid (22:4, ω-6).

The polyunsaturated fatty acids of the ω-3 series may be chosen especially from α-linolenic acid (18:3 ω-3), stearidonic acid (18:4 ω-3), eicosapentaenoic acid or EPA (20:5 ω-3), docosahexaenoic acid or DHA (22:6 ω-3) and docosapentaenoic acid (22:5 ω-3).

α-Linolenic acid, γ-linolenic acid, stearidonic acid, eicosapentaenoic acid, docosahexaenoic acid, mixtures thereof or extracts comprising them will be most particularly suitable for use in the invention.

The sources of γ-linolenic acid may be chosen from plant oils, for instance evening-primrose oil, borage oil, blackcurrant pip oil, Ecchium oil and hemp oil, and extracts of the microalga spirulina (*Spirulina maxima* and *Spirulina platensis*).

Plant oils from walnut, hazelnut, almond (*Juglans regia*), coriander, soybean (*Glycina max*), rapeseed (*Brassica naptus*), chia, flax, musk rose and fish oils, for example, are rich in polyunsaturated fatty acids of the ω-3 series. ω-3 polyunsaturated fatty acids may also be found in zooplankton, crustaceans/molluscs and fish.

Fish oils are the main industrial source of EPA and DHA.

Microalgal biomass may also constitute a raw material for the extraction of ω-3 unsaturated fatty acids.

Thus, a polyunsaturated fatty acid may be used in a composition of the invention in the form of at least one oil chosen from evening-primrose oil, borage oil, blackcurrant pip oil, walnut oil, soybean oil, fish oil, sunflower oil, wheat germ oil, hemp oil, fenugreek oil, musk rose oil, Ecchium oil, argan oil, baobab oil, rice bran oil, sesame oil, almond oil, walnut oil, hazelnut oil, chia oil, flax oil, musk rose oil, olive oil, avocado oil, safflower oil, coriander oil and/or oil extracted from microalgal biomass (for example spirulina) or extracted from zooplankton.

According to one embodiment, a composition of the invention may comprise additional hydrophilic active agents. Hydrophilic active agents that may be used include proteins or protein hydrolysates, amino acids, polyols, especially of $C_2$ to $C_{10}$, for instance glycerol, sorbitol, butylene glycol or polyethylene glycol, urea, allantoin, sugars and sugar derivatives, water-soluble vitamins, starch, and bacterial or plant extracts, for instance those from *Aloe vera*.

According to another embodiment, a composition of the invention may also comprise a lipophilic active agent. Lipophilic active agents that may be used include retinol (vitamin A) and derivatives thereof, tocopherol (vitamin E) and derivatives thereof, ceramides and essential oils.

Process

According to another of its aspects, the present invention relates to an oral cosmetic nailcare treatment process, which may especially be performed by administering the cosmetic compositions as defined above, according to the usual technique for the use of these compositions.

According to one embodiment, the invention relates to an oral cosmetic process for preventing and/or treating nail impairments, in the case of an individual in need thereof, comprising at least one step of administering to said individual, as an active agent, at least one monounsaturated fatty acid, a salt thereof and/or an ester thereof, and in particular petroselinic acid.

A process according to the invention may comprise a step that consists in observing a reduction in, or even disappearance of, the nail impairments.

Advantageously, the application of a process of the invention may reinforce, improve or even restore the growth, the hardness, the resistance to impacts, a physiological form, a smooth appearance, a translucent appearance, or a uniform tint or color, especially a white tint or color.

A cosmetic process according to the invention may be performed especially by administering a food composition as defined above.

A process of the invention may be performed on a daily basis, for example, for instance at a rate of one administration per day or one administration twice a day, for example once in the morning and once in the evening, or three times a day, in particular with each meal.

A cosmetic process according to the invention may be performed, for example, by daily administration of a composition formulated, for example, in the form of gel capsules, sugar-coated tablets, emulsions, tablets, capsules or oral vials, in appropriate amount and number, depending on their form.

An effective amount of monounsaturated fatty acid may be administered in a single dose per day or in fractional doses over the day, for example two to three times a day.

A process according to the invention may advantageously comprise a single administration.

A cosmetic process may be performed over a time period ranging from one week to several weeks, or even several months, this period moreover possibly being repeated after periods without treatment, for several months or even several years.

By way of example, the administration of a monounsaturated fatty acid according to the invention may be performed at a rate, for example, of three times a day more generally over a prolonged period of at least 4 weeks, or even 4 to 15 weeks, optionally comprising one or more periods of interruption or being repeated after a period of interruption.

According to a preferred embodiment, the present application relates to the cosmetic use, via the oral route, of at least one monounsaturated fatty acid, a salt thereof and/or an ester thereof, as a nailcare active agent, said monounsaturated fatty acid being chosen from petroselinic acid, sapienic acid, cis-8-octadecenoic acid and cis-vaccenic acid, or mixtures thereof, and is preferably petroselinic acid.

According to a preferred embodiment, the present application relates to a cosmetic treatment process for nailcare, via the oral route, in the case of an individual in need thereof, comprising at least one step of administering to said individual, as an active agent, at least one monounsaturated fatty acid, a salt thereof and/or an ester thereof, said monounsaturated fatty acid being chosen from petroselinic acid, sapienic acid, cis-8-octadecenoic acid and cis-vaccenic acid, or mixtures thereof, and is preferably petroselinic acid.

FIGURES

FIG. 1: Profile for fatty acid in methyl ester form (FAME) in samples of hair, nails and sebum showing the presence of a complex mixture (left-hand FIGURE) of cis-octadecenoic acid isomers, comprising petroselinic acid (cis-6 18:1), the monounsaturated fatty acid cis-8 18:1, oleic acid (cis-9 18:1) and cis-vaccenic acid (cis-11 18:1). The analysis was performed on a capillary column having as stationary phase an ionic liquid SLB-IL 111 (Supelco). The mixture of standards containing cis-6 16:1, cis-6 18:1, cis-8 18:1 and cis-5, cis-8 18:2 fatty acids was obtained from Lipidox (Sweden).

In the description and the examples that follow, unless otherwise mentioned, the percentages are weight percentages and the ranges of values written in the form "between . . . and . . . " include the stated lower and upper limits. The ingredients are mixed, before being formed, in the order and under conditions that may readily be determined by a person skilled in the art.

The examples below are presented as non-limiting illustrations of the field of the invention.

EXAMPLES

Example 1

Demonstration of petroselinic acid in the Nails a—Materials and Methods

2-Amino-2-methyl-1-propanol was obtained from Sigma-Aldrich (Saint-Louis, USA) and methanol/HCl (3N) was obtained from Supelco (Bellefonte, Pa.).

The methyl esters of pure cis-6 16:1, cis-6 18:1, cis-8 18:1 and cis-5, cis-8 18:2 fatty acids were obtained from Lipidox (Sweden).

The hair, nail and surface skin samples were collected from volunteers (n=6) according to the procedure described below.

Sampling of hair: approximately 20 hairs including the hair follicles were taken from the scalp of women, using tweezers. The hairs were then chopped with a razor blade to obtain about 1 cm of hair from the hair follicle. The hairs including the hair follicle were then combined in a 15 ml Falcon tube before methylation.

Sampling of nails: 1 to 2 mm of nail were cut off with scissors from each of the ten fingers of an individual and combined in a 15 ml Falcon tube before methylation.

Sampling of surface skin: samples of surface skin were collected using the "tape-stripping" method. This method is usually used to study the physiology of the stratum corneum (SC). The SC is a surface layer of the epidermis, which consists of corneocytes inserted in a lipid bilayer. Among these lipids are those produced by the sebum.

Briefly, strips of adhesive tape 2 cm wide and 5 cm long were used (Scotch Magic™ tape). The adhesive tapes were applied to the skin of the right cheek of the volunteers, rubbed gently to ensure adhesion, and pulled off rapidly and abruptly. This procedure was repeated 10 times on the same area. The 10 samples of adhesive tape were combined in a 50 ml Falcon tube and subjected to the extraction process.

The fatty acid methyl esters were prepared as follows. The hair and nail samples (>20 mg) were placed in a mortar and ground finely under refrigerated conditions (liquid nitrogen). The crushed samples were then transferred into 10 ml test tubes with methanol (2 ml), methanol/HCl (2 ml, 3N) and hexane (1 ml). After vigorous stirring, methylation was performed at 100° C. for 60 minutes and the tubes were stirred vigorously every 20 minutes. After cooling to room temperature, water (2 ml) was added and the tubes were centrifuged at 1200 g for 5 minutes. If necessary, the sample was also concentrated before analysis by gas chromatography (GC).

Before methylation, the sebum samples were extracted from the adhesive tapes by immersion and homogenization in hexane (1 ml) and methanol (2 ml) for 1 minute. After removal of the adhesive tapes from the tubes, methanol/HCl (2 ml, 3N) was added and methylation was performed as indicated above.

The 4,4-dimethyloxazoline (DMOX) derivatives for the GC-MS analysis (GC coupled to a mass spectrometer) were prepared as described previously, with a slight modification (Fay et al., J. Chromatogr. A, 1991, 541:89).

Briefly, the FAMEs were dried in the presence of nitrogen and mixed with 2-amino-2-methyl-1-propanol (0.5 ml) and heated at 190° C. overnight. After cooling to room temperature, hexane (2 ml) and water (2 ml) were added, and the tube was stirred vigorously and then centrifuged at 1000 rpm for 2 minutes. The organic phase was recovered and the hexane was evaporated off using nitrogen. The sample was diluted in fresh hexane and analyzed by GC-MS.

The gas chromatography coupled to mass spectrometry (GC-MS) was performed as follows.

The DMOX samples were analyzed on a 6890 Series II gas chromatograph (Agilent Technologies, Santa Clara, Calif.) coupled to a 5973N selective quadrupole mass detector (Agilent Technologies, Santa Clara, Calif.) equipped with a source of ions for electron ionization (EI). The device was operated in positive ion mode using a standard electron energy of 70 eV.

The GC injector was operated in "split" distribution mode: (25:1 distribution ratio) at 250° C., the GC-MS interface was maintained at 250° C. Helium was used as vector gas, at a constant flow rate of 1 ml/minute.

The oven temperature program was: 60° C. at isotherm for 5 minutes, then increased to 160° C. in increments of 15° C./minute, then maintained at isotherm for 1 minute at this temperature, then increased to 195° C. in increments of 2° C./minute, then maintained at isotherm for 1 minute, then increased to 250° C. in increments of 5° C./minute, and maintained at isotherm for 8 minutes.

The electron-ionization mass spectra were recorded in the 50-400 m/z range.

b—Results

The analysis of the FAMEs prepared from the hair, nail and sebum samples was performed using the direct methylation protocol with an acid catalyst at high temperature as described by Destaillats et al. (Lipid Technology, 2004, 16: 183).

The analysis of the FAMEs by GC using the SLB-IL 111 capillary column shows two peaks eluting before methyl oleate. Similar results were obtained with the sebum and nail samples (FIG. 1).

Co-chromatography experiments were performed using a pure standard of petroselinic acid (cis-6 18:1) and of cis-18 18:1 fatty acid.

The results show that the two peaks eluting before methyl oleate have a similar retention time to the cis-6 18:1 and cis-8 18:1 fatty acid isomers.

These data indicate that the hair, nail and sebum lipids contain petroselinic acid.

An analysis of the EI mass spectra of the pure standards confirmed the results obtained by co-chromatography with pure standards and demonstrated the presence of the cis-6 16:1, cis-6 18:1, cis-8 18:1 and cis-5, cis-8 18:2 acids in the hair, sebum and nails.

The length of the chains and the number of double bonds in the fatty acids were deduced from the molecular ions.

In conclusion, the data presented above reveal for the first time the presence of petroselinic acid in nails.

Example 2

Evaluation of the Effect of a Food Supplement Versus Placebo on Nail Quality

A study was carried out on 132 individuals divided up into 2 parallel groups (each of the 2 groups of individuals is divided up by randomization):
a group of 66 individuals receiving the placebo, and
a group of 66 individuals receiving the food supplement to be studied.

The food supplement to be studied is a soft capsule containing 200 mg of coriander oil and made of fish gelatin. The capsules are to be swallowed with a glass of water three times a day, i.e. a capsule with each meal. The ingested dose is 600 mg of coriander oil per day.

The placebo is a soft capsule containing medium-chain triglycerides (caprylic acid) and made of fish gelatin. The capsules are to be swallowed with a glass of water three times a day, i.e. a capsule with each meal.

The treatment is administered for 168 days.

The efficacy parameters measured consist of a self-evaluation of the nail quality.

The study is carried out as a monocentric, double-blind, randomized, comparative study, in parallel groups, versus placebo, on healthy ambulatory individuals. Each individual is randomized with equal probability in one of the following two groups:

Group 1: 66 individuals receiving the placebo.
Group 2: 66 individuals receiving the supplement to be studied.

At the end of the treatment, a self-evaluation of nail quality by the individuals is carried out by means of a visual score, graded from 1 to 6 (with cursor at each score without guidance) regarding the following items:

| Do you consider that your nails are: | |
|---|---|
| Not very or not at all Fragile (1) | Very fragile (6) |
| Very shiny (1) | Not very or not at all shiny (6) |
| Not very or not at all striated (1) | Very striated (6) |
| Very hard (1) | Not very or not at all hard (6) |
| Do you consider that your fingernails split: | |
| Rarely (1) | Frequently (6) |

The results of the study reveal that the nails are less fragile, shinier and harder.

Example 3

Oral Compositions

Example 3A: Powder Stick

| Active ingredient | |
|---|---|
| *Lactobacillus paracasei* ST11 | $10^{10}$ cfu |
| *Bifidobacterium lactis* Bb12 | $10^{10}$ cfu |
| Calcium citrate | 50 mg |
| Petroselinic acid | 420 mg |

| Excipient | |
|---|---|
| Xanthan gum | 0.8 mg |
| Sodium benzoate | 0.2 mg |
| Maltodextrin | qs 30 g |

One stick per day can be taken.

Example 3B: Powder Stick

| Active ingredient | |
|---|---|
| Magnesium gluconate | 50 |
| *Lactobacillus paracasei* ST11 | $5.10^8$ cfu |
| *Bifidobacterium lactis* Bb12 | $5.10^8$ cfu |
| Calcium citrate | 200 |
| Coriander oil | 600 |

| Excipient | |
|---|---|
| Xanthan gum | 0.8 mg |
| Sodium benzoate | 0.2 mg |
| Maltodextrin | qs 30 g |

One stick per day can be taken.

Example 3C: Capsule

| Active principle | mg/capsule |
|---|---|
| Coriander seed oil | 200 |
| Vitamin C | 60 |
| Magnesium stearate | 0.02 |

One to three of these capsules can be taken per day.

Example 3D: Formulation of Sugar-coated Tablet Type

| | mg/sugar-coated tablet |
|---|---|
| Active materials | |
| Coriander seed oil | 600 |
| Excipient for the core of the sugar-coated tablet | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Colorant | 5 |

Example 3E: Formulation of Sugar-coated Tablet Type

|  | mg/sugar-coated tablet |
|---|---|
| Active materials | |
| Coriander seed oil | 600 |
| *Lactobacillus johnsonii* | 10⁹ cfu |
| Excipient for the core of the sugar-coated tablet | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Colorant | 5 |

The invention claimed is:

1. A cosmetic nailcare method for treating brittle, fragile, soft or split nails, or nails which have a dull appearance, the method comprising:
administering, via the oral route, coriander seed oil as an active agent to an individual in need thereof,
wherein the coriander seed oil contains petroselinic acid, the content of which is such that the daily dose of petroselinic acid ranges from 80 to 1000 mg/d.

2. The method as claimed in claim 1, wherein the coriander seed oil is used in combination with at least one additional cosmetic active agent selected from the group consisting of vitamin $B_3$, vitamin $B_5$, vitamin $B_6$, vitamin $B_8$, vitamin C, vitamin E, carotenoids, curcuminoids, flavonoids, orthosilicic acid and monomethylsilanetriol.

3. The method as claimed in claim 1, wherein the coriander seed oil is used in combination with at least one additional cosmetic active agent selected from the group consisting of:
one or more divalent mineral cations,
bacteria or bacterial extracts derived from non-photosynthetic and non-fructifying filamentous bacteria,
probiotic microorganisms,
prebiotic nutrients, and
a mixture of probiotic microorganisms and of prebiotic nutrients.

4. The method as claimed in claim 3, wherein the probiotic microorganism is selected from the group consisting of microorganisms of the genus *Lactobacillus* sp. and/or *Bifidobacterium* sp., a fraction thereof and/or a metabolite thereof.

5. The method as claimed in claim 1, wherein the coriander seed oil is administered 1 to 3 times per day.

6. The method as claimed in claim 1, wherein the coriander seed oil is administered as the sole nailcare active agent.

7. The method as claimed in claim 1, wherein the content of the petroselinic acid in the coriander seed oil is such that the daily dose of petroselinic acid ranges from 160 to 1000 mg/d.

* * * * *